United States Patent [19]

Osanai et al.

[11] Patent Number: 5,026,283

[45] Date of Patent: Jun. 25, 1991

[54] CAPSULES FOR TOOTH-RESTORING MATERIALS

[75] Inventors: Satoshi Osanai, Kawajima; Manabu Hiraoka, Fujimi, both of Japan

[73] Assignee: G-C Dental Industrial Corporation, Tokyo, Japan

[21] Appl. No.: 361,705

[22] Filed: Jun. 1, 1989

Related U.S. Application Data

[63] Continuation of Ser. No. 74,028, Jul. 16, 1987, abandoned.

[30] Foreign Application Priority Data

Aug. 8, 1986 [JP] Japan ................................ 61-185140

[51] Int. Cl.$^5$ ................................................ A61C 5/04
[52] U.S. Cl. ................................... 433/90; 222/136; 206/222; 206/63.5; 604/87
[58] Field of Search ................... 222/80, 81, 82, 86, 222/87, 136, 145; 206/219, 222, 63.5; 433/90; 604/82, 87, 88, 91, 56, 232, 234, 416

[56] References Cited

U.S. PATENT DOCUMENTS

| | | | |
|---|---|---|---|
| 2,754,590 | 7/1956 | Cohen | 433/90 |
| 3,595,439 | 7/1971 | Newby | 604/87 |
| 3,684,136 | 8/1972 | Baumann | 604/416 |
| 3,739,947 | 6/1973 | Baumann et al. | 222/136 |
| 4,064,879 | 12/1977 | Leibinsohn | 604/218 |
| 4,159,570 | 7/1979 | Baskas et al. | 206/222 |
| 4,648,532 | 3/1987 | Green | 604/87 |

FOREIGN PATENT DOCUMENTS 1215477 11/1959 France ................................ 222/136

Primary Examiner—Gene Mancene
Assistant Examiner—Adriene B. Lepiane
Attorney, Agent, or Firm—Oblon, Spivak, McClelland, Maier & Neustadt

[57] ABSTRACT

A capsule for a tooth-restoring material includes a cylinder containing therein the predetermined amount of a powder component of the tooth-restoring material and fitted at its rear end with an extruding plunger; a breakable package held in front of an extreme end opening in the cylinder, the package containing therein an amount of a liquid component of the tooth-restoring material and having its cylinder-facing side formed of a weak material; and a member for holding the package having a nozzle at its outermost end; wherein at a position of the plunger corresponding to the extreme end opening in the cylinder is provided a member capable of breaking through the package of a size small enough not to close up the opening and the nozzle, when the plunger moves to and reaches the package-holding member.

11 Claims, 2 Drawing Sheets

CAPSULES FOR TOOTH-RESTORING MATERIALS

This application is a Continuation of application Ser. No. 07/074,028, filed on Jul. 16, 1987, now abandoned on Jun. 1, 1989.

BACKGROUND OF THE INVENTION

1. Field of the Invention

The present invention relates to a capsule for a tooth restoring material, which is used when the tooth-restoring material consisting of liquids and powder, two components are used for filling, fitting, relining, filling-up or other tooth restoration.

2. Statement of the Prior Art

In general, tooth-restoring materials are filled for the restoration of tooth cavities. Such tooth-restoring materials are usually based on two components which react easily with each other by mixing. The two-component materials often comprise a combination of powders and liquids, which are now put on the market, while filled in glass or plastic bottles. Such two-component materials should be filled in cavities as rapidly as possible prior to curing, since their curing reaction proceeds immediately upon mixing.

The manipulations for weighing and mixing together the aforesaid bottled materials with a spatula just prior to filling are troublesome and time consuming. Hence, there have recently been commercially available capsules in which a certain amount of powders and liquids is contained in an isolated state. Such capsules dispense with any weighing manipulation, and mixing of the two components upon combined together is finished within several seconds by applying mechanical vibrations thereto.

Even with the capsules in which the pre-weighed amounts of tooth-restoring materials are contained, a considerable time is still required to fill them in cavities, since the thus mixed content should first be transferred to a separate vessel. In particular, the curing reaction of the mixed tooth-restoring materials proceeds more rapidly at elevated temperatures. Thus, not a few failures occur, because such curing reaction have already proceeded to a some extent at the time of filling.

We have made various studies to solve the problems as mentioned above and, as disclosed in Japanese Utility Model Application No. 60(1985)-201319, have proposed a syringe assembly of extruding the tooth-restoring material contained in a capsule. Immediately upon mixing of the tooth-restoring material contained in the capsule, that syringe assembly is attached to the capsule to allow rapid pouring thereof into a tooth cavity through a nozzle fitted to the tip of the capsule without either interfering with the visual examination of a narrow region to be restored in the mouth cavity or applying pressure to a patient.

The development of such a syringe assembly has enabled the tooth-restoring material mixed in the capsule to be rapidly filled in the region to be restored. However, there are still problems of wherein the tooth-restoring material consisting of powders and liquids and contained in the associated capsule in an isolated state, the package with the liquid components being filled therein in pre-located in the capsule, or how the liquid component of the package is mixed with the powder component and guided to the tooth region to be restored.

For instance, we take a capsule comprising a dental formulation-mixing container of such a structure as disclosed in Japanese Utility Model Publication No. 55(1980)-46625. A package containing therein the liquid component of the tooth-restoring material and breakable by giving pressure thereto (hereinafter called a breakable package) is positioned on the side of the cylinder. The overall configuration of the package is thus complicated from the need of providing an additional location for mounting a clip for holding the package on the side of the cylinder. The presence of such a clip leads to a further disadvantage that the diameter of the capsule is larger than required. Furthermore, a pin must be attached to the tip of the cylinder to prevent an outflow of the tooth-restoring material mixed, thus rendering the manipulation more troublesome.

SUMMARY OF THE INVENTION

We have now found that, if a breakable package containing therein the liquid component of a tooth-restoring material and having its one side formed of a weak material is positioned between an opening in the extreme end of a cylinder and a nozzle attached thereto, it is not required to locate a clip-mounting portion on the side of the cylinder, as taught in Japanese Utility Model Publication No. 55-46625, and the mixed tooth-restoring material is prevented from flowing out of the nozzle, unless two sheets forming the breakable package are damaged.

According to the present invention, there is provided a capsule for a tooth-restoring material, including a cylinder containing therein the predetermined amount of a powder component of said tooth-restoring material and fitted at its rear end with an extruding plunger; a breakable package held in front of an extreme end opening in said cylinder, said package containing therein an amount of a liquid component of said tooth-restoring material and having its cylinder-facing side formed of a weak material; and a member for holding said package having a nozzle at its outermost end; wherein at a position of said plunger corresponding to said extreme end opening in said cylinder is provided a member capable of breaking through said package of a size enough not to close up said opening and said nozzle, when said plunger moves to and reaches said holding member.

DETAILED DESCRIPTION OF THE DRAWINGS

Figure 1:
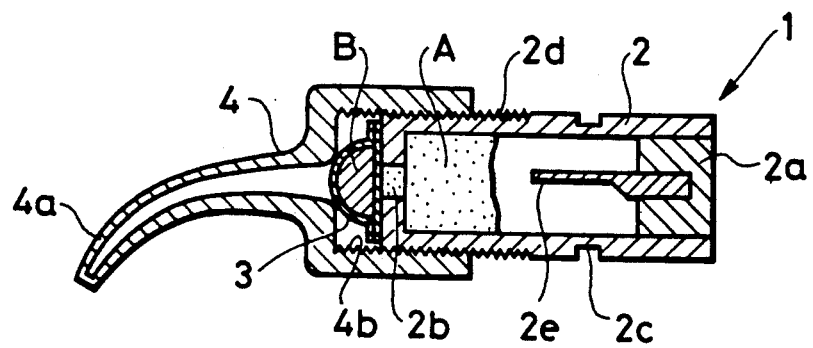
Figure 2:
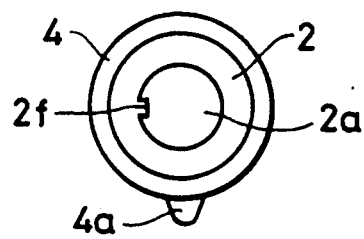
Figure 3:
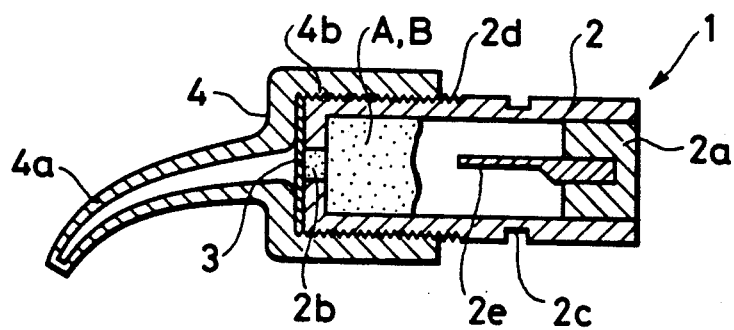
Figure 4:
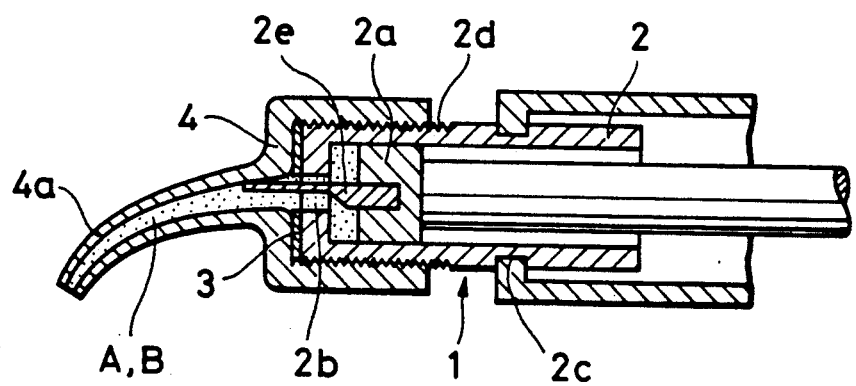
Figure 5:
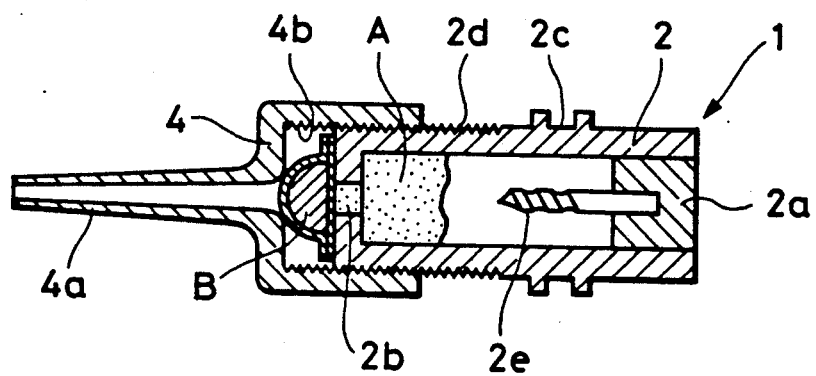

For a better understanding of the present invention, several embodiments of the capsule according to the present invention will now be described in greater detail, by way of example, with reference to the accompanying drawings, in which:

FIG. 1 is a side section of one preferred embodiment of the capsule for tooth-restoring materials according to the present invention, FIG. 2 is a right-hand side view of that embodiment, FIG. 3 is a side section showing the tooth-restoring material contained in the capsule of FIG. 1, which is now mixed together, FIG. 4 is a side section illustrating the tooth-restoring material which is now extruded out of the nozzle from the state of FIG. 3, and FIG. 5 is a side section similar to FIG. 1, which shows another embodiment of the capsule for tooth-restoring materials according to the present invention.

DETAILED DESCRIPTION OF THE PREFERRED EMBODIMENTS

In the drawings, a capsule for a tooth-restoring material according to the present invention is generally shown at 1. A cylinder 2 contains therein the predetermined amount of a powder component A of the tooth-restoring material, and is fitted at its rear end with an extruding plunger 2a. At an end thereof opposing the plunger 2a, there is an opening 2b. The cylinder 2 is provided around its outside with a recess 2c for engagement with a syringe for extruding the tooth-restoring material, which is not shown for simplicity, and includes an male thread 2d around its extreme end. It is understood that the cylinder 2 may be provided around its inside with a guide 2f in a keyed or other form for the purpose of restricting the rotation of the extruding plunger. Preferably, the cylinder 2 is constructed from a transparent or semi-transparent material such as plastics or glass to ensure easy sight of the tooth-restoring material contained therein. Most preferably, it is construced from plastics hard to be damaged during transportation or when dropped accidentially. A breakable package 3 to be located further in front of the opening 2b in the cylinder 2 and containing therein a liquid component B of the tooth-restoring material has the cylinder 2-facing side formed of a weak material such as an aluminium foil and the opposite side of a material such as a plastic coated aluminium foil having a strength higher than that of said weak material. A package-holding member 4 is located still further in front of the opening 2b in the cylinder 2 to hold the package on its weak side, and has a nozzle 4a at the outermost end. The package-holding member 4 is internally threaded for threaded engagement with the outer periphery of the cylinder 2. In one instance, the nozzle 4a of the package-holding member 4 has its center line extending in parallel with the center axis of the cylinder 2. In the other instance, center line is curved with respect to the center axis of the cylinder 2. Further, the extreme end of the nozzle 4a of the package-holding member 4 may be open from the outset, whereas it may be cut out for opening at the time of use. In the former instance, the nozzle 4a may be provided over its open end with a pin or lid-like member so as to prevent entrance of foreign matter therethrough. In the latter instance, the extreme end of the nozzle 4a may previously be formed therearound with a mark such as an indent or line for indicating the area to be cut out. In accordance with the present invention, at a position of the plunger 2a corresponding to the opening 2b in the cylinder 2, there is a package breaking-through member 2e of a size enough not to close up the opening 2b in the cylinder 2 and the nozzle 4a of the package-holding member 4, when the plunger 2a moves to and reaches the package-holding member 4. The package breaking member 2e has a length in the direction of movement of the plunger 2a is greater than the thickness of the package 3 in that direction.

Reference will now be made to how to use the capsule for a tooth-restoring material according to the present invention, which is of the structure as explained above.

First, the female thread 4b of the package-holding member 4 is screwed into the male thread 2d of the cylinder 2 of the present capsule 1, thereby applying pressure to the breakable package 3. Thereupon, the weak material of the package 3 is broken out to cause the liquid component B therein to flow in the cylinder 2 through its opening 2b. Just upon the liquid component B entering the cylinder 2, it is mixed with the powder component A of the tooth-restoring material previously contained in the cylinder 2 by means of an exclusive mixer ready for this purpose. Immediately after mixing of the components A and B has been made in this manner, the recess 2c of the capsule 1 is engaged with and attached to the syringe for the tooth-restoring material. As the plunger of that syringe moves forward the plunger 2a of the cylinder 2, the breaking-through member 2e provided at the extreme end of the plunger 2a, i.e., at the end of the plunger 2a facing the package-holding member 4, passes through the opening 2b in the cylinder 2 and breaks through the unbroken, strong material of the package 3 facing the cylinder 2, whereby the mixed tooth-restoring material begins to flow in the nozzle 4a of the package-holding member 4. In this manipulation manner, where the nozzle 4a of the package-holding member 4 is closed up at its open end previously or by a pin or lid-like member, the closed-up portion of the nozzle 4a is forced open, or the pin or lid-like member is removed. The extreme end of the nozzle 4a may then be guided to the tooth cavity to be restored to fill the tooth-restoring material therein.

In the capsule assembly for a tooth-restoring material according to the present invention as mentioned above, it is unnecessary for an operator to weigh the powder and liquid components A and B of the tooth-restoring material for each use, since they are contained therein by the predetermined amounts in an isolated state. Further, since the breakable package 3 containing the liquid component B of the tooth-restoring material is positioned at the extreme end of the cylinder 2, it is very unlikely that the diameter of the cylinder 2 may be increased, as is the case with Japanese Utility Model Publication No. 55-46625. Therefore, when the present capsule is attached to the syringe for the tooth-restoring material and inserted in the mouth cavity to fill that material in a tooth cavity, it does not interfere at all with the visual examination of the mouth cavity state. In addition, with the present capsule it is possible to mix together the tooth-restoring material with no fear of an outflow thereof from the nozzle provided at its outermost end. These and other features of the present capsule make a great contribution to dentistry.

We claim:

1. A capsule for a tooth restoring material, comprising:
   a cylinder containing therein a predetermined amount of a powder component of the tooth restoring material;
   plunger slidably fitted in one end opening of said cylinder;
   a breakable package having a face formed of a weak material covering another end opening of said cylinder and containing therein an amount of a liquid component of the tooth restoring material, whereby said face formed of a weak material may be ruptured to mix said liquid and powder components;
   a member having a nozzle and being positioned relative to said cylinder such that said package is held between said member and said cylinder; and
   a package breaking member mounted on said plunger for movement therewith and having a length in the direction of movement of said plunger which is greater than a thickness of said package in said direction of movement, wherein said nozzle, said another end opening and said package breaking member are aligned and sized such that said package breaking member may break said package, pass through said another end opening and enter said nozzle during advancement of said plunger towards said another end opening for dispensing the mixed liquid and powder components, said package breaking member being smaller in width than said nozzle by an amount such that said package breaking member does not close said another end opening and said nozzle during the advancement of said plunger toward said another end opening.

2. A capsule as recited in claim 1, wherein said cylinder is formed of plastics.

3. A capsule as recited in claim 1, wherein said cylinder includes around its outside a recess for engagement with a syringe for extruding said tooth-restoring material.

4. A capsule as recited in claim 1, wherein said cylinder includes an internal guide for restricting rotation of said plunger.

5. A capsule as recited in claim 1, wherein said weak face of said package is formed of aluminum foil.

6. A capsule as recited in claim 1, wherein said nozzle has a center line extending in parallel with a center axis of said cylinder.

7. A capsule as recited in claim 1, wherein said nozzle has a center line curved with respect to a center axis of said cylinder.

8. A capsule as recited in claim 1, wherein an outermost end of said nozzle is open.

9. A capsule as recited in claim 1, wherein an outermost end of said nozzle is closed and formed of a material which may be cut for opening at a time of use.

10. A capsule as recited in claim 1, wherein said package breaking member includes around its outside a groove of a spatula shape in cross section.

11. A capsule as recited in claim 1, wherein said package breaking member includes around its outside a groove of a spiral shape in cross section.

* * * * *